(12) United States Patent
McDonald

(10) Patent No.: US 6,270,514 B1
(45) Date of Patent: Aug. 7, 2001

(54) SENSITIVE ADJUSTMENT FORCEPS APPARATUS

(75) Inventor: Henry H. McDonald, Rancho Mirage, CA (US)

(73) Assignee: Surgical Concepts, Inc., Newport Beach, CA (US)

( * ) Notice: Subject to any disclaimer, the term of this patent is extended or adjusted under 35 U.S.C. 154(b) by 0 days.

(21) Appl. No.: 09/480,618

(22) Filed: Jan. 10, 2000

(51) Int. Cl.[7] .............................. A61B 17/50; A61F 9/00
(52) U.S. Cl. ............................................ 606/210; 606/107
(58) Field of Search .................................. 606/205, 206, 606/208, 210, 133, 151, 157, 158; D28/55; D24/143; 294/99.2; 433/159; 451/389; 81/7, 308, 303, 307, 312, 318; 29/243.56; 24/455, 461, 492, 513, 515, 568

(56) References Cited

U.S. PATENT DOCUMENTS

| | | | |
|---|---|---|---|
| 902,726 | * 11/1908 | Greer | 294/99.2 |
| 2,533,801 | * 12/1950 | Heilig | 606/210 |
| 5,236,436 | * 8/1993 | Koros et al. | 606/148 |
| 5,292,324 | * 3/1994 | McDonald | 606/107 |
| 5,776,139 | * 7/1998 | McDonald | 606/107 |

* cited by examiner

*Primary Examiner*—Henry J. Recla
*Assistant Examiner*—Tan-Uyen T. Ho
(74) *Attorney, Agent, or Firm*—William W. Haefliger (57) ABSTRACT

Apparatus used for manipulation of a gripped element employed in surgery, which includes two elongated arms, each of which has a distal first zone, a second zone or zones rearward of the distal first zones, and a handle from which the arms extend forwardly, the arms extending so that the first distal zones are yieldably urged toward one another by the arms to hold the gripped element therebetween, at least one of the arm second zones configured to move relative to the other arm in response to controllable force exertion between and along the arms, thereby to cause the first zones to relatively separate, enabling gripping or release of the element.

35 Claims, 7 Drawing Sheets

SENSITIVE ADJUSTMENT FORCEPS APPARATUS

BACKGROUND OF THE INVENTION

This invention relates generally to forceps apparatus with sensitive adjustment, and more specifically, concerns improvements in surgical forceps instruments responsive to finger pressure.

There is continual need for improvements in surgical forceps adjustability and sensitivity to manual adjustment; and in particular for improvements as are described herein, to provide unusual advantages as will appear.

SUMMARY OF THE INVENTION

It is a major object of the invention to provide improved instrumentation meeting the above-described need.

Basically, the herein-described apparatus is used for manipulation of a gripped element employed in surgery, which includes:
   a) two elongated lever arms, each of which has a distal first zone, and a second zone or zones rearward of said distal first zone, and a handle from which the arms extend forwardly,
   b) the arms extending so that the first distal zones are yieldably urged toward one another by the arms to hold the gripped element therebetween,
   c) at least one of the arm second zones configured to move relative to the other arm in response to controllable force exertion between the arms, thereby to cause such first zones to relatively separate, enabling gripping or release of the element.

As will be seen, the gripped element may be positioned between the forceps arm first distal zones, to be released or gripped in response to arm pivoting. In an example, the gripped element may comprise an artificial lens to be inserted into the eye, positioned, and released.

Another object is to provide a device located externally of the eye and in association with the arms to exert force on the arms causing arm release of the element in the eye. Such a device may, in one preferred form, comprise a pusher having camming engagement with at least one of the arms, at the second zone or zones. The pusher may be carried or positioned between the arms, for such camming engagement, as for example with slide camming surfaces of both arms.

A further object is to provide a space between the arms, to receive the pusher; and a space may also be provided to receive the user's finger usable to push the pusher, for adjusting the spreading of the arms, in infinitely and sensitively adjustable manner. If desired, a spring may be provided to yieldably urge the pusher in a position restoration direction.

An additional object is to provide a method of manipulating an element to be gripped for use in surgery, which includes
   a) providing two elongated lever arms, each of which has a distal first zone, and a second zone or zones rearward of the distal first zone, and providing a handle from which the arms extend forwardly,
   b) the arms supported so that the first distal zones are yieldably urged toward one another by the arms to hold the gripped element therebetween,
   c) at least one of the arm second zones configured to pivot relative to the other arm in response to controllable force exertion between the arms,
   d) and exerting controlled force between the arms to cause at least one arm to move relative to the other arm for enabling gripping or release of the element by the first distal zones.

As referred to, an arm pusher may be provided via which such controllable force is applicable to the arms to cause at least one arm to pivot relative to the other arm; and the pusher may be positioned between the second zones of the two arms to have sliding engagement with the arms, in response to finger pressure.

A yet further object is to exert controllable force on the pusher to cause the pusher to controllably and relatively spread the arms in response to sliding engagement therewith, and with space provided between the arms to receive the user's finger to operate the pusher. The method may also include accurate release of the element, such as an artificial lens, in the eye, by exerting highly sensitively adjustable force on the pusher externally of the eye.

A further object is to provide for pusher camming engagement with at least one of the arms so as to provide mechanical advantage whereby pusher displacement by an amount $d_1$ exceeds relative spreading of the two arm distal zones by an amount $d_2$, expressed as $d_1 > d_2$.

Another object is to provide finger slide surfaces extending longitudinally along the arms at said second zones, said surfaces tapering laterally toward a longitudinally elongated space between said arms. Such slide surfaces may typically include first and second slide surfaces at opposite sides of the elongated space. The arms may also define third and fourth slide surfaces at opposite sides of the elongated space, the first and third slide surfaces located on one of said two arms, and said second and fourth slide surfaces located on the other of said two arms. The arms may also define laterally extending domes extending longitudinally along the respective arms, said slide surfaces located proximate said domes, respectively. Accordingly, finger pressure may be exerted against the slide surface, as between the domes, and while displacing the loci of finger pressure longitudinally along said surfaces to controllably effect separation of said arm distal zones.

These and other objects and advantages of the invention, as well as the details of an illustrative embodiment, will be more fully understood from the following specification and drawings, in which:

DRAWING DESCRIPTION

FIG. 9 views a)–d), show progressive stages of lens release, in side view;

DETAILED DESCRIPTION

Figure 1:
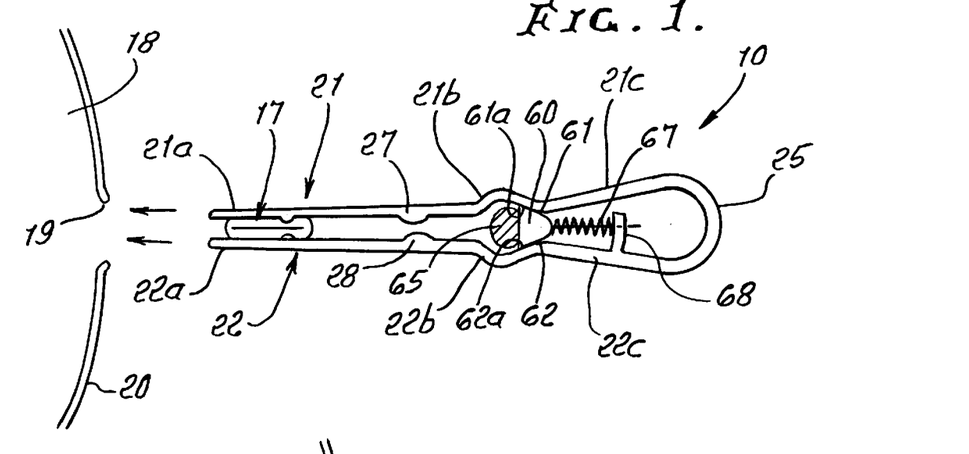
FIG. 1 is a side elevation showing a preferred embodiment, and an element or object gripped by the device.
Figure 2:
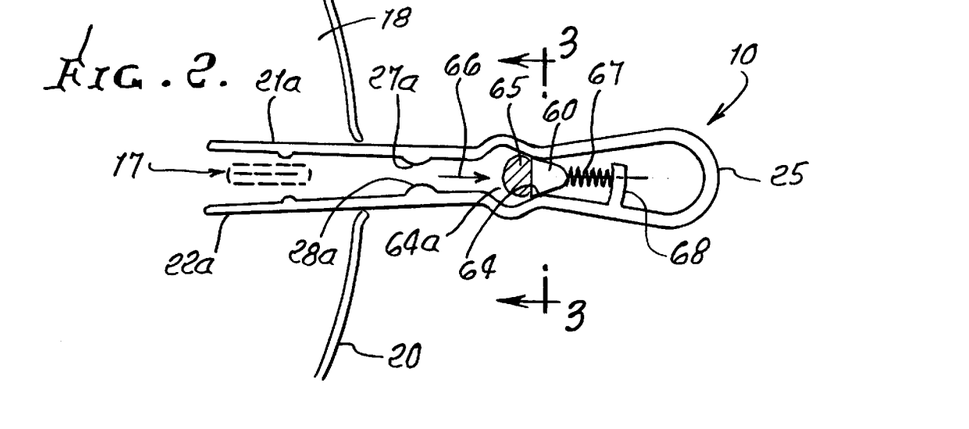
FIG. 2 is a view like FIG. 1 but showing manual force application to cause element release.
Figure 3:
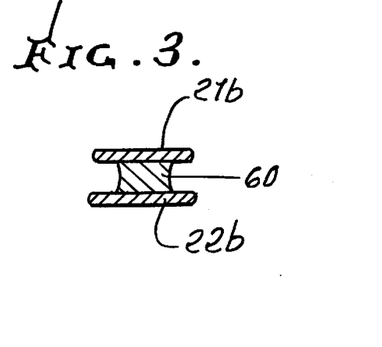
FIG. 3 is a section taken on lines 3—3 of FIG. 2.
Figure 10:
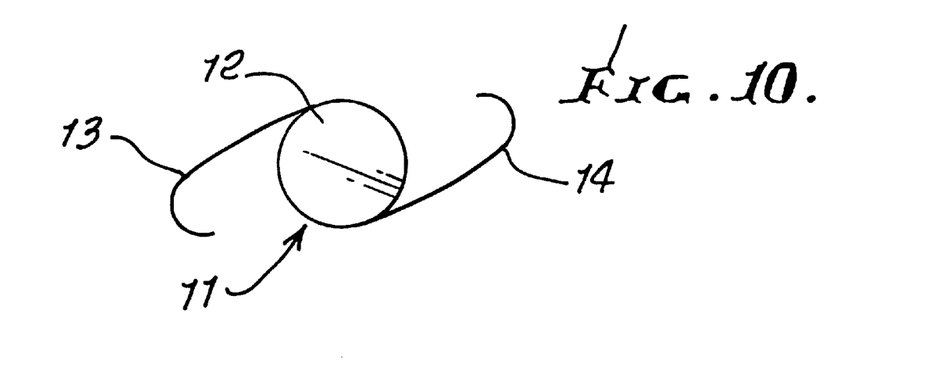
FIGS. 10 and 11 show lenses with different haptics.
Figure 11:
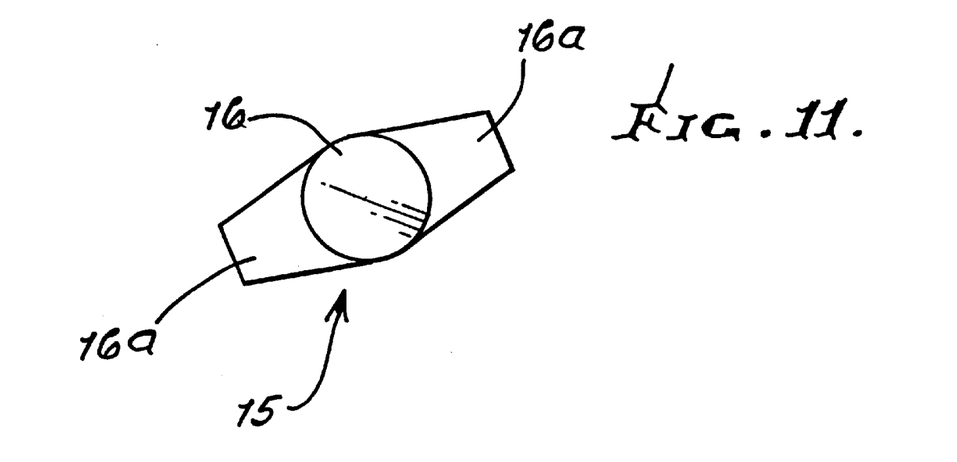

In FIGS. 1 and 2, the device or apparatus 10, i.e. instrument, is used for intraocular implantation of a plastic lens. Typical lens units are shown in FIGS. 10 and 11, others being usable. See for example my U.S. Pat. Nos. 5,203,789, 5,203,790 and 5,425,759, incorporated herein by reference.

In FIG. 10, a lens unit 11 has a lens zone 12, and two filamentary haptics 13 and 14.

In FIG. 11, the lens unit 15 has a lens zone 16, and two tabular or plate-like haptics 16a, for centering the unit in the eye.

Figure 1A:
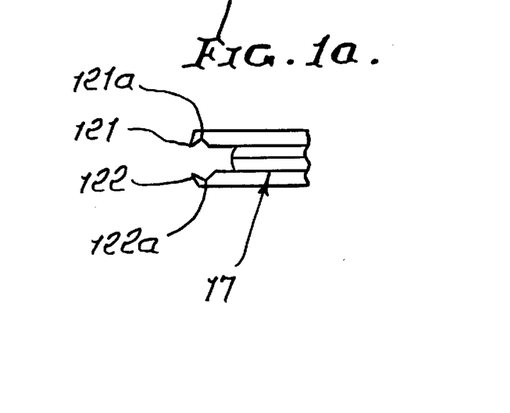
FIG. 1a is an enlarged view showing arms having angled grippers at their terminal ends.

A single folded lens unit is shown at 17 in FIG. 1, to be implanted in the eye interior 18 via a surgical incision 19 in the corneo-scleral limbus 20. The folded lens is gripped between and by two elongated lever arms 21 and 22. Arm 21 has a distal first zone 21a, and arm 22 also has a distal first zone 22a; and the lens is gripped between those arm zones. As also shown in FIG. 1a the arms may also have irregular grips 121 and 122 angled and tapering inwardly toward one another at the arm ends for enhanced positive claw action gripping of elements such as a lens or pieces of eye structure to be inserted into the eye, or withdrawn from the eye. More precise positioning of the gripped element relative to eye structure is thereby achieved. Also note recesses 121a and 122a.

Arm 21 also has a second zone 21b rearward of and spaced from the distal zone 21a; and a handle zone 21a rearward of and spaced from the zone 21b. Likewise, arm 22 has a second zone 22b rearward of and spaced from zone 22a, and a handle zone 22c rearward of and spaced from zone 22b. Arm zones 21b and 22b are typically angularly deviated from one another.

The arm handles are typically coupled together rearwardly of said zones 21b and 22b so that the first distal zones 21 and 21b are yieldably urged toward one another by the arms to lightly but firmly grip the lens therebetween for implantation, as seen in FIG. 1. As shown, the arms are interconnected by bowed spring metal segment 25 at the rearward extents of the handles. Accordingly, the arms are supported so that the first distal zones are yieldably urged toward one another by the arms to hold the gripped element therebetween.

In accordance with the invention, at least one of the arm second zones, and preferably both second zones, are configured to pivot or spread apart relative to the other arm in response to controllable force exertion between the arms. In the example, a device, such as a pusher seen at 60, is located in association with the arms, and is finger operable externally of the eye, to exert force on the arms causing arm spreading, as seen in FIG. 2, for releasing the previously gripped lens element 17, in the eye. Further, the pusher 60 has camming engagement with at least one of the arms, at the second zone referred to. see pusher tapered camming surfaces 61 and 62, in slidable engagement with tapering arm surfaces 61a and 62a, to cause gradual and precisely controlled spreading apart of the arms, and of the first distal zones 21a and 22a, in FIG. 2. The released surgical object, such as an artificial lens is shown at 17a, within the eye.

Further, it will be seen that, preferably, the slidable camming engagement of the pusher with the arms provides a mechanical advantage whereby pusher displacement by an amount $d_1$ exceeds relative spreading of the two arm distal zones by an amount $d_2$, expressed as $d_1 > d_2$. This means that an enhanced precision of distal zone separation, to release or grip the object 17, is achieved, and in a simple and highly effective manner.

It will also be seen that the arm second zones 21b and 22b are configured, for example bowed as shown, to provide a space 64 between 21b and 22b to receive the pusher, as shown; and further another space 64a, or a continuation of space 64, is provided to receive the user's finger 65, for operating the pusher—i.e. pushing at rightwardly or rearwardly, in the direction of arrow 66, as the handles 21a and 22a are held or manually gripped.

Also shown is a compression spring 67 acting to urge the pusher leftwardly or forwardly, when finger pushing pressure is relieved, i.e. to allow restoration of the arms to the position seen in FIG. 1, by arm spring return action. As shown, compression spring 67 is located between the rear of the pusher, and a tang 68 on one arm, helping to position or carry the pusher. The pusher may have modified delta Δ shape, as shown, i.e. with two slide surfaces and one finger pressure receiving surfaces.

Figure 7:
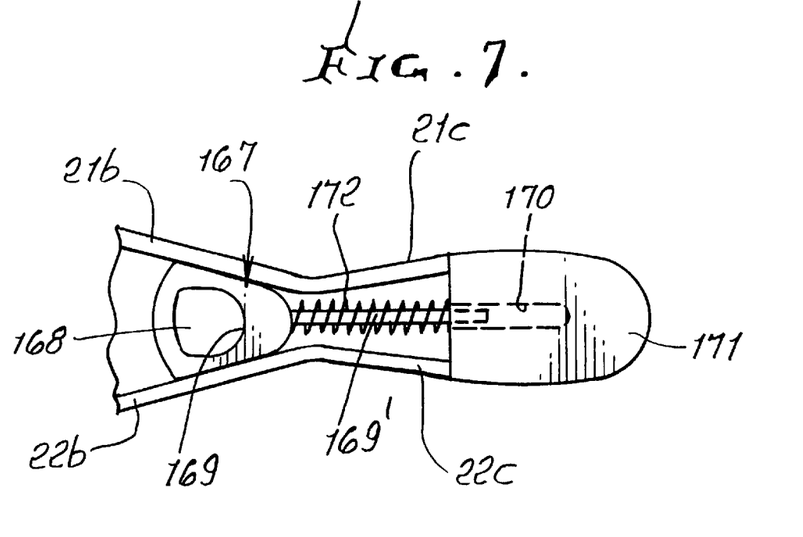
FIG. 7 is a fragmentary view of a modification in which alternate pushing surfaces are provided on the device pusher.
Figure 8:
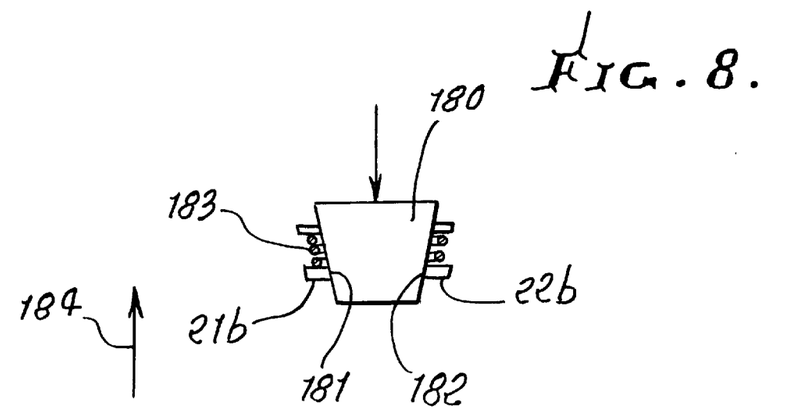
FIG. 8 is a fragmentary view showing a further modified pusher.
Figure 9A:
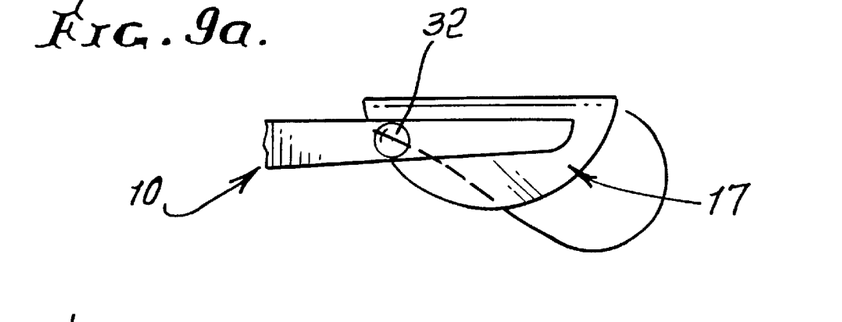
Figure 9B:
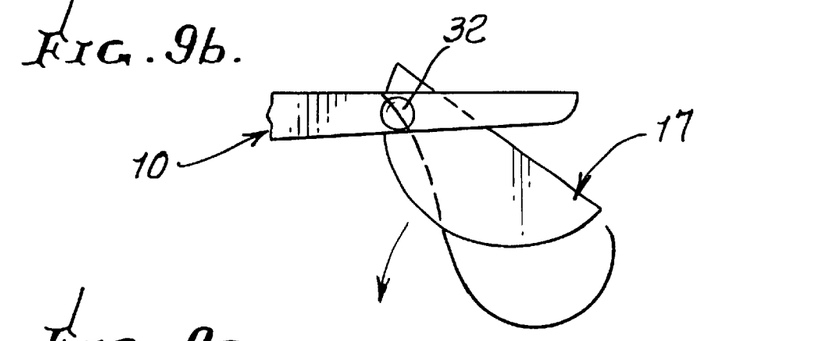
Figure 9C:
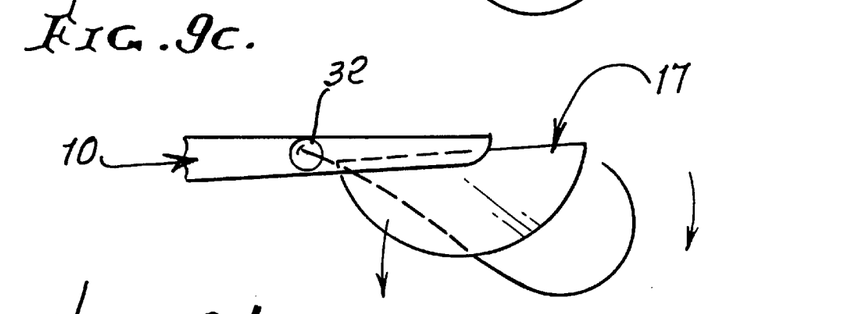
Figure 9D:
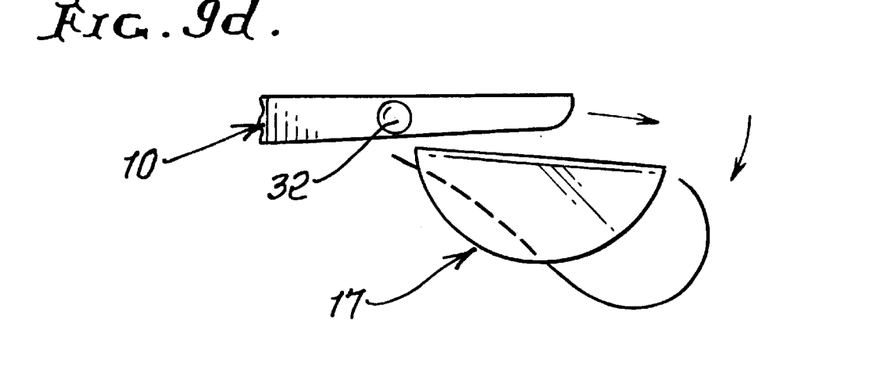

FIG. 7 shows a modified pusher 167 having a recess 168 to receive the user's finger tip, to exert rearward pressure at recess shoulder 169. A pin 169 extends from the pusher to guide in a bore 170 formed by solid handle part 171 carrying the arm handles 21c and 22c. Compression spring 172, like spring 67, is confined between the pusher and the part 171. In FIG. 8, the pusher 180 is carried to be pushed downwardly between the arms 21b and 22b in camming engagement with the arms, at 181 and 182, to controllably spread them. See also return springs 183 acting on the pusher to urge it upwardly, in a direction indicated by arrow 184.

In the example shown in FIG. 1 and 2, there are interenageable protrusions or stops 27 and 28 projecting between the arms at the second zones, to limit squeezing of lens 17 by arm zones 21a and 22a, during arm pivoting. The protrusions, which may be integral with the arms, have interengageable surfaces 27a and 28a which are convex toward one another, and are spaced apart, as seen in FIG. 1. If the pusher is deactivated, i.e. pushed forward or outward, squeezing of the arms rearwardly of the protrusions brings the surfaces 27a and 28a into interengagement, followed by rocking apart of the arm forward distal portions 21a and 21k, to allow lens release. The protrusions are close enough together that the lens is not damaged by slightly increased gripping force exertion thereon just prior to interengagement of the rocking protrusions, and subsequent lens release.

FIG. 9, steps a), b), c) and d), show progressive positions of a typical lens 17 as it releases from the instrument 10. Pivot point protrusions 32 and 33 from the arms engage the opposite sides of the gripped lens, and act as fulcrums, for lens pivoting, as it is released and without damage to the lens. The arms 21 and 22 are shown to have substantially the same configurations that are mirror imaged with respect to a central plane 40. Note that the arms remain at opposite sides of that plane, i.e., they do not cross over one another.

Figure 4:
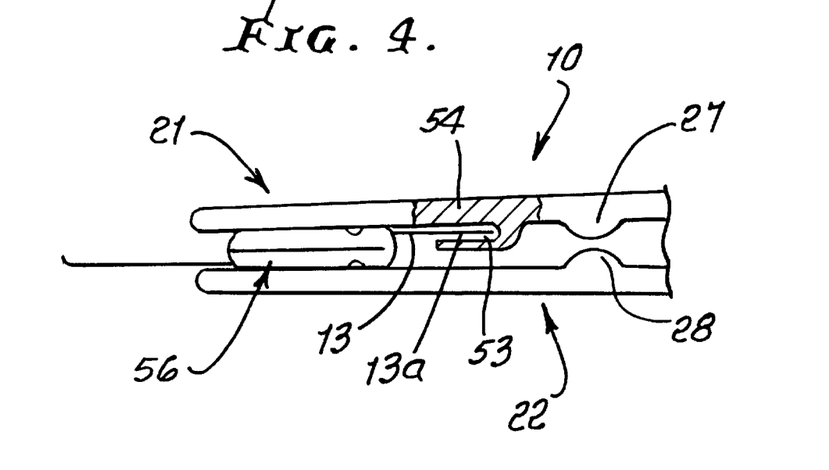
FIG. 4 is an enlarged fragmentary view of a modification showing retention of a haptic projecting from a lens gripped by the device.

A modification may be provided wherein arm 21 has a small recess 53 formed in arm inner portion 54, for receiving the end portion 13a of a lens filamentary haptic 13, as referred to above. This controls the rear haptic position, as during lens implantation, and overcomes the problem of follow-up insertion of the rear haptic into the eye, after the lens itself has been positioned. As the released lens pivots away from the arms 21 and 22, the "trapped" rear haptic extent 13*a* moves out of the recess 53 and into desired position in the eye. If desired, recess 53 can be located in a protrusion 27 or 28. A single folded lens 56 is shown in FIG. 4.

Figure 5:
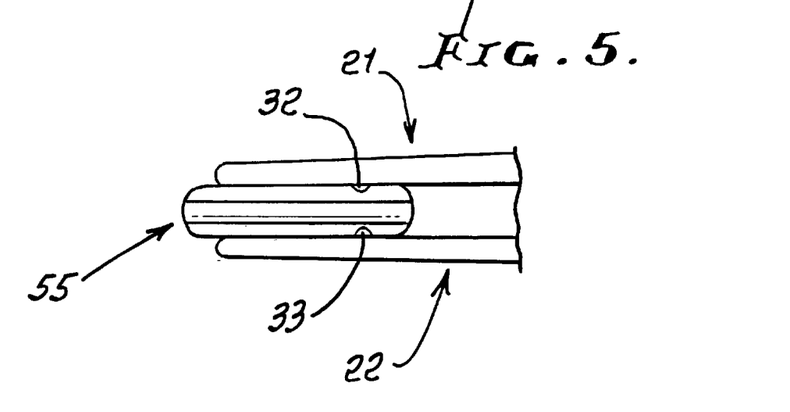
FIG. 5 is an enlarged fragmentary view showing gripping of a lens, which has multiple folds.
Figure 6:
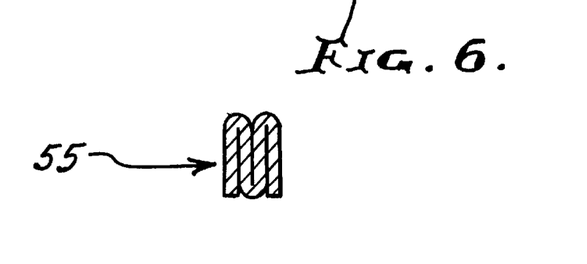
FIG. 6 is a section taken through the multiple folded lens of FIG. 5.

FIGS. 5 and 6 show a multiple folded lens 55 having M or W shape, as seen in FIG. 6. FIG. 5 shows that lens gripped by the instrument arms 21 and 22.

The method of use includes
  a) providing two elongated lever arms, each of which has a distal first zone, and a second zone or zones rearward of said distal first zone, and providing a handle from which said arms extend forwardly,
  b) said arms supported so that said first distal zones are yieldably urged toward one another by said arms to hold the gripped element therebetween,
  c) at least one of said arm second zones configured to pivot relative to the other arm in response to controllable force exertion between the arms,
  d) and exerting controlled forced between the arms to cause said at least one arm to pivot relative to the other arm for enabling gripping or release of said element by said first distal zones.

Figure 12:
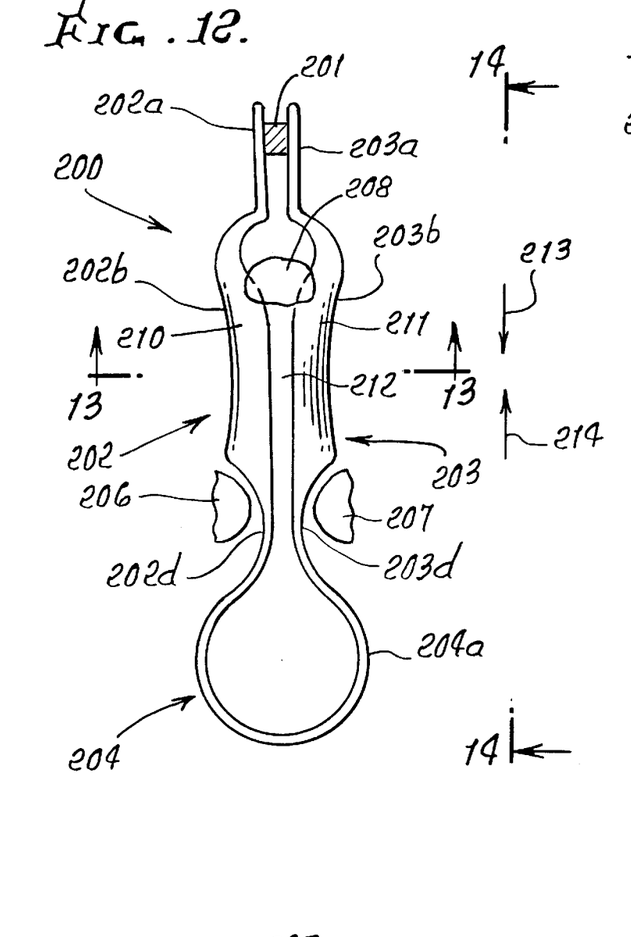
FIG. 12 is a view like FIG. 1 showing a modified instrument.
Figure 13:
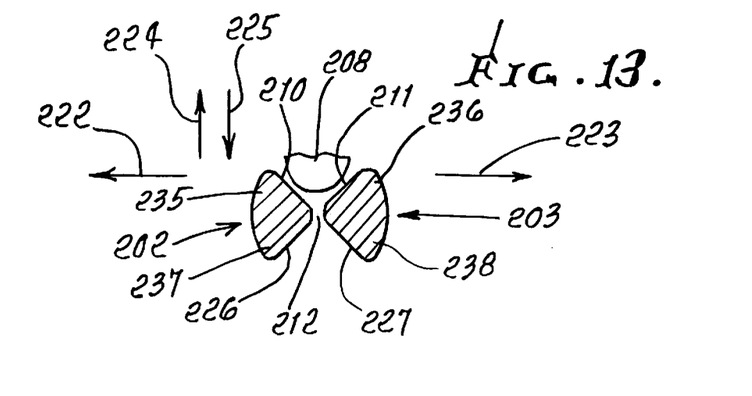
FIG. 13 is an enlarged section taken on lines 13—13 of FIG. 12.
Figure 14:
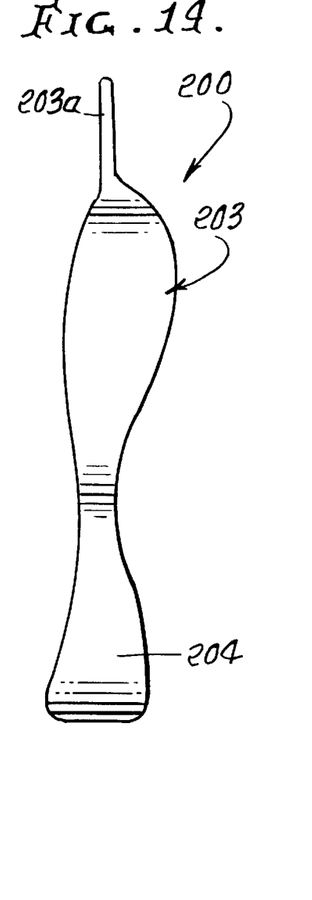
FIG. 14 is a side view taken on lines 14—14 of FIG. 12.

Referring to FIGS. 12–14 modified apparatus 200, which may be regarded as one preferred form, is useful for manipulation of a gripped element 201, as may for be employed in surgery. One example is an artificial lens to be introduced into the eye.

The apparatus includes:
  a) two elongated lever arms 202 and 203, having distal first zones 202*a* and 203*a*; second or intermediate zones 202*b* and 203*h* rearward of the first zones; and a handle 204 from which the arms extend forwardly; and
  b) the first distal zones 202*a* and 203*a* being yieldably urged toward one another by the arms 202 and 203, to hold the gripped element 201 between the distal zones, and
  c) at least one of the arm second zones configured to move relative to the other arm in response to controllable force exertion between the arms, thereby to cause the first zones to relatively separate, enabling gripping or release of the element 201.

Handle 204 may include a bow spring 204*a* that loops as shown, and is joined to or is integral with arm zones 202*b* and 203*k*, to yieldably urge the arms toward one another. The user's fingers (or one finger and one thumb) 206 and 207 may be applied to outward facing recesses 202*d* and 203*d* in the arms to hold them in a position for manipulation by another finger 208, as for example the forefinger.

As shown, there are finger slide surfaces extending and elongated longitudinally along the arms at said second zones, the surfaces tapering laterally toward a longitudinally elongated space between said arms. See for example, opposed first and second slide surfaces 210 and 211 which taper laterally and inwardly toward longitudinally elongated space 212 between 202*b* and 203*b*. The taper is such that the user's forefinger can be controllably moved in a longitudinal direction 213, in engagement with surfaces 210 and 211 to locally and controllably move or push the arms apart, or in opposite direction 214, to controllably allow the arms to move relative toward one another under the influence of the bow spring 204*a*. A high mechanical advantage is achieved, for very accurate control of element 201 gripping by projecting distal ends of the arms at 202*a* and 203*a*, as during surgery; that is, for a finger longitudinal displacement $d_1$, the lateral displacement $d_2$ of the distal zones (to widen or reduce the gap therebetween) is such that $$d_1 >> d_2$$

One example is
$d_1$ is over 3 times $d_2$

Note that the arms at and along zones 202*b* and 203*b* are thickened laterally, in directions 222 and 223; and also upwardly and downwardly, in directions 224 and 225, as indicated in FIGS. 12 and 13. This facilitates greater finger control and finger handling of the instrument.

If desired, the slide surfaces may include third and fourth slide surfaces at opposite sides of said elongated space, such first and third slide surfaces located on one of the two arms, and the second and fourth slide surfaces located on the other of said two arms. See for example surfaces 226 and 227 which are located at the under or opposite sides of the arms relative to surfaces 210 and 211. As shown, the first and second slide surfaces taper downwardly toward said space 212; and the third and fourth slide surfaces taper upwardly toward said space. As also shown, the arms define laterally extending first and second domes extending longitudinally along the respective arms, said first and second slide surfaces located proximate said first and second domes, respectively See for example domes 235 and 236, in FIG. 13. The arms also define downwardly and laterally extending third and fourth domes extending longitudinally along the respective arms, said third and fourth slide surfaces located proximate the said first and second domes, respectively. See for example domes 237 and 238.

The method of use of the FIGS. 12–14 instrument includes:
  a) providing two elongated lever arms, each of which has a distal first zone, and a second zone or zones rearward of said distal first zone, and providing a handle from which the arms extend forwardly,
  b) the arms extending so that the first distal zones are yieldably urged toward one another by the arms to hold the gripped element therebetween,
  c) at least one of the arm second zones configured to move relative to the other arm in response to controllable force exertion between the arms,
  d) and exerting slidably controlled force between the arms to cause said at least one arm to move relative to the other arm for enabling gripping or release of said element by said first distal zones.

The method may typically also include providing finger slide surfaces extending longitudinally along the arms at said second zones, such surfaces tapering laterally toward a longitudinally elongated space between said arms.

Figure 15:
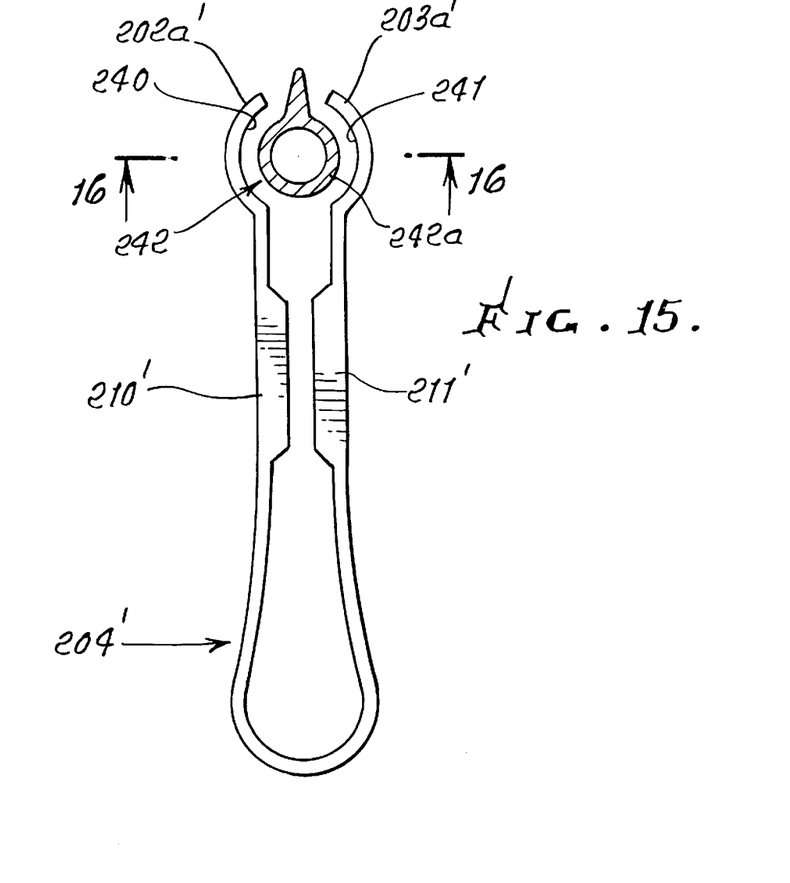
FIG. 15 is a view like FIG. 1 showing another modified instrument.
Figure 16:
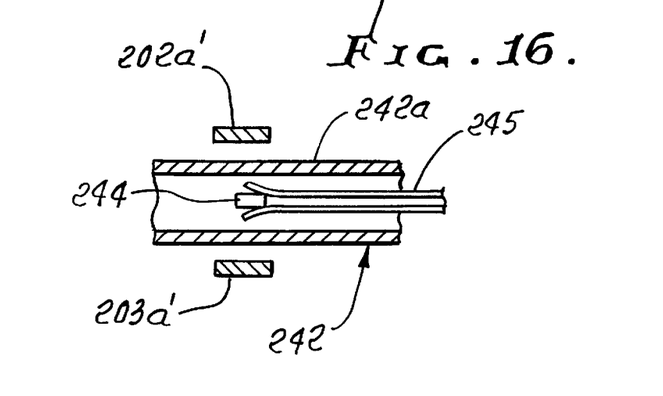
FIG. 16 is a section taken on lines 16—16 of FIG. 15.

FIGS. 15 and 16 show a modified instrument, with elements corresponding to those of FIGS. 12–14 bearing the same numbers, primed. The modified arm distal zones 202*a*' and 203*a*' have concave inner surface 204 and 241, facing the gripped element 242, for gripping its cylindrical outer surface 242*a*. That element may comprise another surgical instrument, such as a small diameter tube, via which an intraocular lens 244 may be inserted into the eye, as via elongated lens holder 245.

The devices of FIGS. 13–15 can be easily made, as by stamping metal sheets, and folding at the handle, to bring the arms into position.

I claim:

1. Apparatus used for manipulation of a gripped element employed in surgery, which includes in combination:

a) two elongated lever arms, each of which has a distal first zone, and a second zone or zones rearward of said distal first zone, and a handle from which the arms extend forwardly, the arms urged toward one another, b) said arms being biased such that said first distal zones are yieldably urged toward one another to hold the gripped element therebetween, c) at least one of said arm second zones configured to move away from the other arm in response to controllable force exertion between said second zones of the arms, thereby to cause said first zones to relatively separate, enabling gripping or release of said element, and d) a Pusher located between said arm second zone or zones for exerting said controllable force, in response to being pushed by a user, and a spring located between said arms for biasing said pusher to relieve said controllable force.

2. The combination of claim 1 including said element positioned between and gripped by said arm first zones.

3. The combination of claim 2 wherein said gripped element and said first distal zones are positioned in the eye.

4. The combination of claim 3 wherein said pusher is located externally of the eye and in association with said arms to exert force on the arms causing arm release of said element in the eye.

5. The combination of claim 4 wherein said pusher has camming engagement with at least one of the arms, at said second zone or zones.

6. The combination of claim 1 wherein the pusher has sliding engagement with at least one of the arms.

7. The combination of claim 1 wherein the pusher has sliding engagement with both of said arms.

8. The combination of claim 1 wherein the arm second zones are located to provide a space therebetween to receive the pusher.

9. The combination of claim 1 wherein the arm second zones are located to provide a space therebetween to receive the user's finger for pushing the pusher.

10. The combination of claim 1 wherein the arm second zones are separated to provide a space therebetween to receive the pusher and the user's finger for pushing the pusher.

11. The combination of claim 1 wherein the spring urges the pusher in a direction to reduce camming force engagement of the pusher with at least one of the arms.

12. The combination of claim 11 wherein the pusher is located directionally between the spring and the arm first distal zones.

13. The combination of claim 5 wherein the pusher camming engagement with at least one of the arms provides mechanical advantage whereby pusher displacement by an amount $d_1$ exceeds relative spreading of the two arm distal zones by an amount $d_2$, expressed as $d_1 > d_2$.

14. The combination of claim 1 wherein there are finger slide surfaces extending longitudinally along said arms at said second zones, said surfaces tapering laterally toward a longitudinally elongated space between said arms.

15. The combination of claim 14 wherein said slide surfaces include first and second slide surfaces at opposite sides of said elongated space.

16. The combination of claim 15 wherein said slide surfaces include third and fourth slide surfaces at opposite sides of said elongated space, said first and third slide surfaces located on one of said two arms, and said second and fourth slide surfaces located on the other of said two arms.

17. The combination of claim 16 wherein said first and second slide surfaces taper downwardly toward said space, and said third and fourth slide surfaces taper upwardly toward said space.

18. The combination of claim 14 wherein each of said arms defines a lateral dome extending longitudinally along each arm, said slide surfaces associated with said domes.

19. The combination of claim 17 wherein said arms define laterally extending first and second domes extending longitudinally along the respective arms, said first and second slide surfaces located proximate said first and second domes, respectively.

20. The combination of claim 17 wherein said arms also define laterally extending third and fourth domes extending longitudinally along the respective arms, said third and fourth slide surfaces located proximate said third and fourth domes, respectively.

21. The combination of claim 20 wherein said arms define concave finger grips located longitudinally of said domes.

22. The method of manipulating an element to be gripped for use in surgery, which includes a) providing two elongated lever arms, each of which has distal first zone, and a second zone or zones rearward of said distal first zone, and providing a handle from which said arms extend forwardly, and are urged toward one another, b) said arms being biased such that said first distal zones are yieldably urged toward one another to hold the gripped element therebetween, c) at least one of said arm second zones configured to move away from the other arm in response to controllable force exertion between said second zone or zones of the arms, d) and exerting controlled force between the arms to cause said at least one arm to move relative to the other arm for enabling gripping or release of said element by said first distal zone, e) there being a pusher located between said arm second zone or zones for exerting said controllable force, in response to being pushed by a user, and a spring located between said arms for biasing said pusher to relieve said controllable force.

23. The method of claim 22 including locating said pusher between said arm second zones to have sliding engagement with the arms.

24. The method of claim 23 including exerting said controllable force on said pusher to cause the pusher to controllably and relatively spread said arms in response to sliding engagement therewith.

25. The method of claim 23 including providing a space between the arm second zones to receive the pusher.

26. The method of claim 23 including providing space between the arm second zones to receive the user's finger for pushing the pusher.

27. The method of claim 23 including providing a space between the arms to receive pusher and also to receive the user's finger for pushing the pusher.

28. The method of claim 22 including providing said element in a gripped position between said first distal zones.

29. The method of claim 28 including manipulating said arms to cause said element to be inserted into the eye via an incision in the eye.

30. The method of claim 29 including releasing said element in the eye by exerting controllable force on the pusher, externally of the eye.

31. The method of claim 28 wherein said element is provided in the form of an artificial lens.

32. The method of claim 22 including providing finger slide surfaces extending longitudinally along said arms at said second zones, said surfaces tapering laterally toward a longitudinally elongated space between said arms.

33. The method of claim 32 wherein said slide surfaces are provided to include first and second slide surfaces at opposite sides of said elongated space.

34. The method of claim 33 including exerting finger pressure against said slide surfaces while displacing the loci of finger pressure longitudinally along said surfaces to controllably effect separation of said arm distal zones.

35. The method of claim 28 wherein said element comprises an elongated tube; and include displacing an artificial lens through said tube.

* * * * *